(12) United States Patent
Noble

(10) Patent No.: US 6,745,395 B2
(45) Date of Patent: Jun. 8, 2004

(54) HAT WITH DISPLAY DEVICE

(75) Inventor: Eileen W. Noble, Brooklyn, NY (US)

(73) Assignee: Noble Tile & Vessel, Inc., Brooklyn, NY (US)

( * ) Notice: Subject to any disclaimer, the term of this patent is extended or adjusted under 35 U.S.C. 154(b) by 178 days.

(21) Appl. No.: 10/032,828

(22) Filed: Oct. 25, 2001

(65) Prior Publication Data

US 2003/0079274 A1 May 1, 2003

(51) Int. Cl.[7] .................................................. A61F 9/00
(52) U.S. Cl. ............................ 2/12; 2/175.1; 2/195.1; 40/586
(58) Field of Search ....................... 2/12, 10, 15, 175.1, 2/175.5, 195.1, 195.2, 175.9, 195.6; 40/586; D2/865–867, 872, 874, 876, 879–882, 884, 886

(56) References Cited

U.S. PATENT DOCUMENTS

| 385,912 | A | 7/1888 | Coote |
|---|---|---|---|
| D36,563 | S | 9/1903 | Collins |
| 824,860 | A | 7/1906 | Grove |
| 829,492 | A | 8/1906 | Spiegel |
| 893,548 | A | 7/1908 | Rosenfeld |
| 942,498 | A | 12/1909 | Heinemann |
| 990,490 | A | 4/1911 | Miller |
| 1,259,297 | A | 3/1918 | Russell |
| 1,274,804 | A | 8/1918 | Spitzer |
| 1,474,572 | A | 11/1923 | Whitstock |
| 1,475,430 | A | 11/1923 | Curwen |
| 1,732,357 | A | 10/1929 | Davis |
| D148,113 | S | 12/1947 | Mandel |
| 2,619,646 | A | 12/1952 | Torricelli |
| 2,704,903 | A | 3/1955 | Laughlin |
| 2,765,472 | A | 10/1956 | Schoen-Wolski |
| 2,766,458 | A | 10/1956 | Schoen-Wolski |
| 2,810,978 | A | 10/1957 | Chapman |
| 2,874,387 | A | 2/1959 | Bannister et al. |
| 3,406,476 | A | 10/1968 | Wilcox |
| 3,484,969 | A | 12/1969 | Newland |
| 3,660,919 | A | 5/1972 | Nagel |
| 3,811,213 | A | 5/1974 | Eaves |
| 3,918,185 | A | 11/1975 | Hasala |
| D244,500 | S | 5/1977 | Copeland |
| 4,057,855 | A | 11/1977 | Hovhannessian |
| 4,187,629 | A | 2/1980 | Yamada |
| 4,202,396 | A | 5/1980 | Levy |
| 4,233,767 | A | 11/1980 | Hryhorczuk |
| 4,255,380 | A | 3/1981 | Björkland |

(List continued on next page.)

Primary Examiner—A. Vanatta
Assistant Examiner—Katherine Moran
(74) Attorney, Agent, or Firm—Brown Raysman Millstein Felder & Steiner LLP

(57) ABSTRACT

Hats such as baseball-type caps and sun visors which have a brim projecting from the forward part of the hat, or sailor hats or Stetson-type (or cowboy-type or fedora-type) hats that have a brim extending about the periphery of the hat are provided with a device on or forming the brim that presents two or more composite graphic images or sets of images. The hat brim includes at least two interleaved series or sets of sections are arranged in a wave-like manner that each present a composite image or a set of images. The sections of each series of interleaved sections generally face in a common direction so that images or parts of images displayed by the sections of a same series are viewable together, and the sections of different series face in different directions. An observer can view a first image or set of images on the brim from a first direction and second image or set of images on the brim from a second direction. For example, the sections of one series of sections may display a composite image of Mickey Mouse, while the sections of another series of sections may display a composite image of Donald Duck, or the sections may display messages, or combinations of graphic objects such as cartoon characters and messages, etc.

27 Claims, 8 Drawing Sheets

U.S. PATENT DOCUMENTS

| | | | |
|---|---|---|---|
| 4,263,737 A | 4/1981 | Simon | |
| D270,319 S | 8/1983 | Greenberg | |
| 4,422,253 A | 12/1983 | Babberl | |
| 4,694,506 A | 9/1987 | Perna | |
| 4,719,651 A | 1/1988 | Tereshinski | |
| 4,937,960 A | 7/1990 | Otake | |
| 4,939,858 A | 7/1990 | Dailey | |
| D359,159 S | 6/1995 | Barker | |
| 5,450,629 A * | 9/1995 | Gilstrap | 2/209.11 |
| D364,507 S | 11/1995 | Schwartz | |
| 5,525,383 A | 6/1996 | Witkowski | |
| 5,598,650 A | 2/1997 | Brown | |
| 5,787,956 A | 8/1998 | Chen | |
| 5,901,484 A | 5/1999 | Seder | |
| 5,903,926 A | 5/1999 | Fleming | |
| D417,063 S | 11/1999 | Henning | |
| 5,991,916 A * | 11/1999 | Sierra | 2/12 |
| 6,133,892 A | 10/2000 | Borgwardt | |
| 6,173,516 B1 | 1/2001 | Duerrstein | |
| D440,382 S | 4/2001 | Scheinbaum | |
| 6,256,796 B1 | 7/2001 | Fleming | |

\* cited by examiner

HAT WITH DISPLAY DEVICE

BACKGROUND OF THE INVENTION

This invention relates generally to caps, hats and head apparel, and more particularly to caps, hats and head apparel having a device that can display various images or messages.

SUMMARY OF THE INVENTION

The invention provides head apparel having a brim (hereinafter referred to simply as a "hat"), such as a baseball-type cap or a sun visor which have a brim projecting from the forward part of the hat, or a sailor hat or Stetson-type (or cowboy-type or fedora-type) hat that have a brim extending about the periphery of the hat, with a device that presents two or more composite graphic images or sets of images for viewing on the brim of the hat. "Image" or "images" are used herein in a broad sense, and encompass images of persons, places, things, characters, figures, graphic designs and abstracts, text, messages, etc., or parts thereof. The invention thereby provides an entertainment or enjoyment value, or commercial value (e.g., advertising, marketing, and promotion) in addition to the value(s) typically presented by a hat. For example, the graphic images can be those of licensed characters, such as those available from The Walt Disney Company and Warner Brothers, for example, or advertisements or marketing or promotional material. The images may also have a personal or other relationship with the person wearing the hat. For example, the images may portray a relative such as a grand parent or grand child, or a place visited by the wearer, or a cause supported by the wearer, or a novelty feature or message such as those typically provided by beer manufacturers. This arrangement can personalize the hat for the holder thereof beyond simple display of a graphic or massage on the cap portion, typically the front thereof, of a baseball-type cap, for example. Hats incorporating the invention may therefore be provided for many purposes, including personalization, enjoyment, entertainment, marketing, promotional, advertising and/or novelty purposes.

The invention provides the two or more graphic images or sets of images, when viewed by an observer from different directions, on or defining a hat brim. "Direction" as used in a broad sense and encompasses linear directions as well as directions along a curve, and clockwise and counter-clockwise directions. The hat brim comprises at least two interleaved series or sets of sections arranged in a wave-like manner such that each present a composite image or a set of images. The sections of each series of interleaved sections generally face in a common direction so that images or parts of images displayed by the sections of a same series are viewable together, and the sections of different series face in different directions. In a preferred embodiment, individual sections of the first series and individual sections of the second series are alternatingly interspersed with the adjacent edges of the sections being parallel. Preferably all or a substantial number of the edges of the sections in the series are parallel.

An observer can view a first image or set of images on the brim from a first direction and second image or set of images on the brim from a second direction. For example, the sections of one series of sections may display a composite image of Mickey Mouse, while the sections of another series of sections may display a composite image of Donald Duck, or the sections may display messages, or combinations of graphic objects such as cartoon characters and messages, etc.

The sections of a series may be pre-printed with an image or part thereof, or they may be constructed so as to be suitable for receiving an image or part thereof that can be affixed to or printed on the sections in any suitable manner. Where the wave-like sections forming a brim, or a structure securable to a brim, are not pre-printed, images may be applied to the wave-like sections. In accordance with the invention, a wave-like structure is provided having the wave-like sections described above, with and without pre-applied images, that can be secured to brims. Where the wave-like sections are securable to a brim, the invention provides means for removably securing the wave-like sections to a brim. The invention also provides kits for applying images to wave-like sections and for applying wave-like sections to brims.

A brim comprising series of sections as described above may be provided for viewing from one side of the brim (one-sided viewing), e.g., from the top, or for viewing from more than one side, e.g., from both sides of the brim (two-sided viewing). For two-sided viewing in a baseball-type cap or a visor, the brim is provided with the wave-like interleaved sections on both the top and bottom of the brim. A brim configured for two-sided viewing can display at least four composite images or sets of images viewable from at least two directions from above the brim and at least two directions from below the brim.

For a Stetson-type hat, or a sailor hat, the brim can extend in a closed loop about the periphery of the hat, which can have wave-like sections extending partially or entirely about the brim, in spaced clusters extending about the brim. The brim can extend generally vertically when the hat is worn, as in the case of a sailor hat, or generally horizontally, as in the case of a Stetson-type hat.

The hat comprises a loop structure sized to engage a person's head and a brim, as described herein, with the wavelike interleaved sections secured to the loop structure as a brim and defining the brim, or secured to a brim panel which in turn is connected to the loop structure of the hat. Thus, the brim may be defined by the wave-like interleaved sections, or the wave-like sections may define structures that are secured to a brim panel on one or more sides thereof. Depending on the embodiment, the loop structure is defined by or comprises either a cap section (e.g., the non-brim portion of a baseball-like hat) or a band (e.g., the non-brim portion of visor-like hat).

The loop structure comprises, for example, a band and may include a cap section or raised part. Images, pictures, text, messages, etc., may be carried by the cap section or a raised part.

The hat brim may have a picture associated therewith as described in application Ser. No. 10/032830 (Attorney Docket No. 4855/4), titled "Picture Matte and Graphic Image Display Device", filed concurrently herewith, the disclosure of which is incorporated herein by reference.

BRIEF DESCRIPTION OF THE DRAWINGS

The foregoing and other aspects of the invention will become more apparent from the following description of illustrative embodiments thereof and the accompanying drawings which illustrate the invention by way of example. In the drawings.

DESCRIPTION OF THE PREFERRED EMBODIMENTS

Figure 1A:
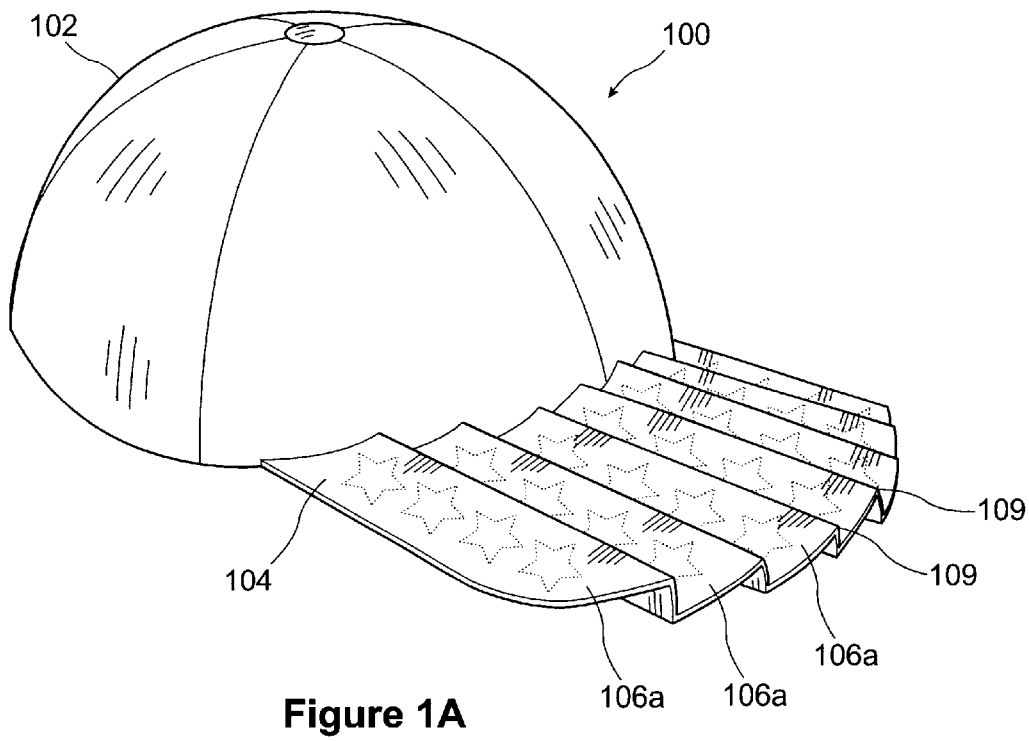
FIG. 1A is a perspective view of the top of a baseball-type cap incorporating the invention showing a series of images on the brim viewed from one side of the cap.
Figure 5:
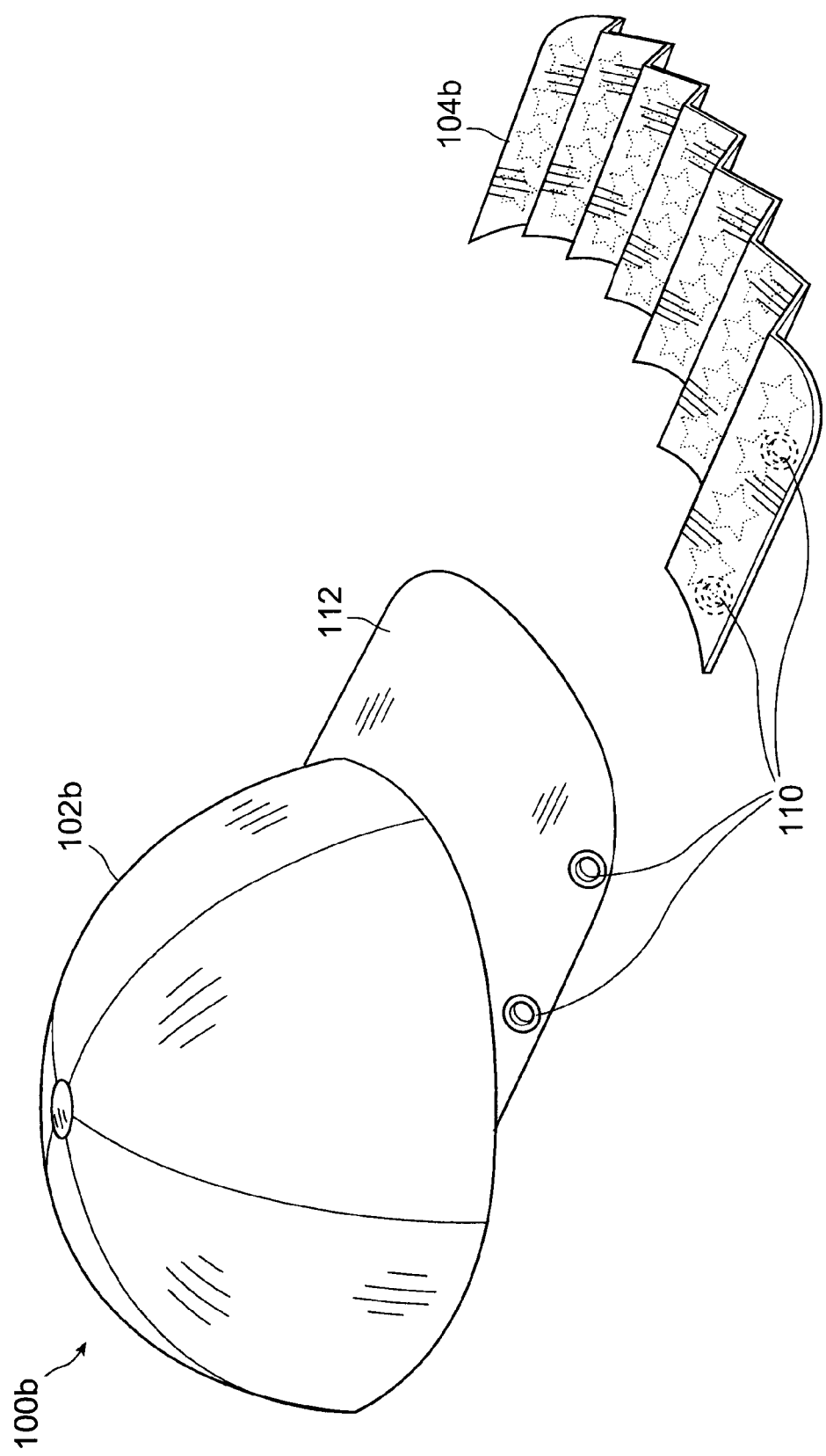
FIG. 5 is an exploded perspective view of a baseball-type cap incorporating the invention in which a wave-like structure is removably secured to the brim.

Referring to FIG. 1A, a baseball-type cap 100 according to the invention comprises a loop structure comprising a cap section 102 and a brim 104 having a wavelike configuration that comprises two interleaved series 106, 108 of sections 106a, 108a suitable for displaying a composite image or a series of images. In this embodiment, the interleaved series 106, 108 define the brim, i.e., the brim does not include an underlying brim panel to which the sections are secured. FIGS. 1A,B, 2A,B, 3A,B and 4A,B,C depict embodiments in which the wave-like structure defines the brim. FIG. 5 depicts an embodiment in which a wave-like structure is removably secured to a brim panel. The brim 104 depicted in FIGS. 1A,B, 2A,B, 3A,B and 4A,B,C defines the brim, as discussed above. However, in the embodiments depicted in those figures, a brim may comprise a brim panel, such as brim panel 112 depicted in FIG. 5, and wave-like structures permanently secured to the brim panel, e.g., by adhesive, heat or sonic welding, mechanical fastener systems, e.g., rivets, staples, etc. A brim panel may be a conventional brim, a stiff panel, e.g., of cardboard or plastic, suitable for supporting one or more wave-like structures.

The sections 106a, 108a are shown to be flat, but may have some other configuration that is also suitable for displaying an image or part of an image, e.g., curved or segmented, etc. The sections 106a of one series face in one direction and the sections 108a of the other series face in another direction, here the opposite direction. Thus, in FIG. 1, all first series sections 106a face in a first same linear direction and all second series sections 108a face in a second same linear direction.

In some embodiments, the cap section 102 may or may not display graphics and/or text, etc., commonly displayed on baseball-type caps. The cap section 102 may be adjustable and is sized to engage and be supported on a person's head.

The wave-like brim 104 may be made of any suitable material, such as stiff fabric, cardboard, fabric covered cardboard, etc., and is sufficiently rigid, per se and/or in cooperation with the manner in which the brim is secured to the loop structure, to maintain the wave-like configuration of the brim.

Referring again to FIG. 1A, the individual first series sections 106a and individual second series sections 108a are alternatingly interspersed with each other so that adjacent first and second series sections 106a and 108a have common edges 109. In the preferred embodiments, the common edges 109 are substantially parallel to each other. The phrase "substantially parallel" as used herein, should be interpreted to mean parallel to the degree necessary so that composite image components can be viewed as a composite image from a suitable direction.

In another embodiment (not shown), adjacent wave-like sections 106a and 108a do not have common edges but have distinct and separated edges. Such edges, however, are also preferably substantially parallel to each other.

Figure 1B:
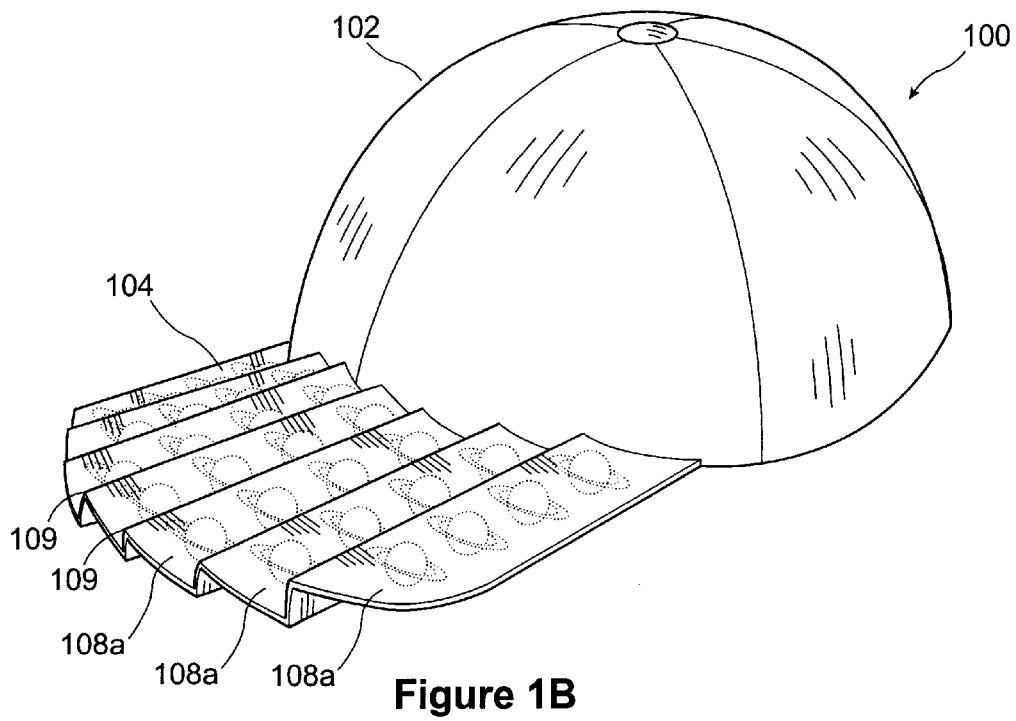
FIG. 1B is a perspective view of the top of a baseball-type cap depicted in FIG. 1A showing another series of images viewed from the opposite side of the cap.
Figure 2A:
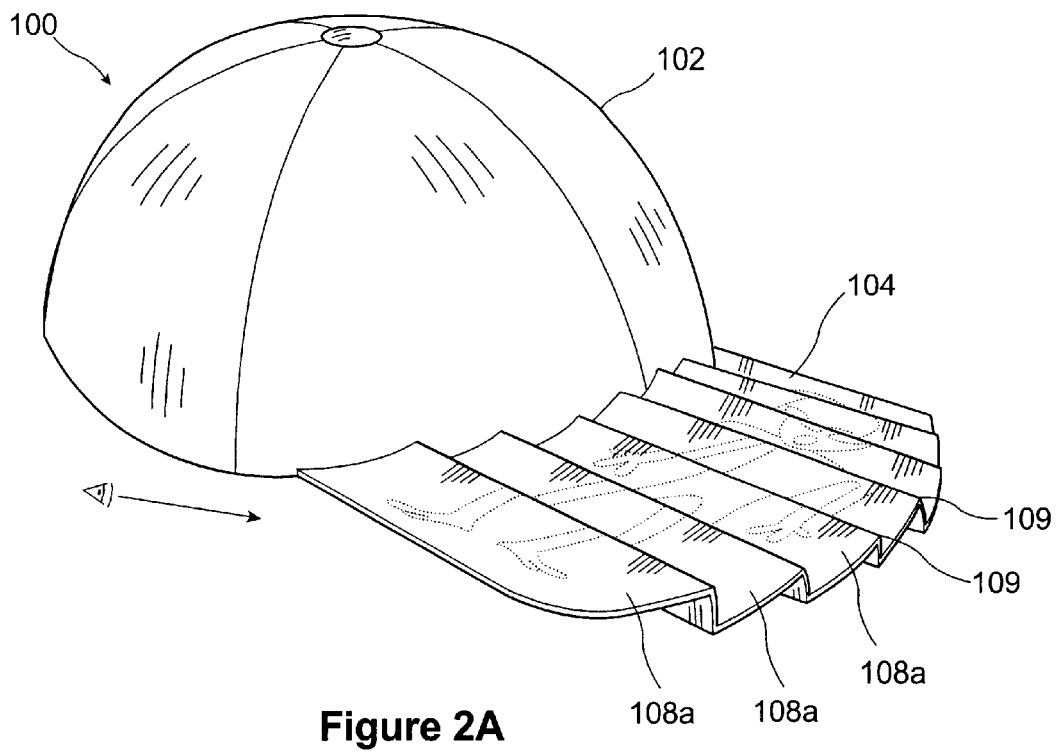
FIG. 2A is a perspective view of the top of a baseball-type cap, similar to the cap depicted in FIG. 1A, incorporating the invention, and showing a composite image on the brim viewed from one side of the cap.
Figure 2B:
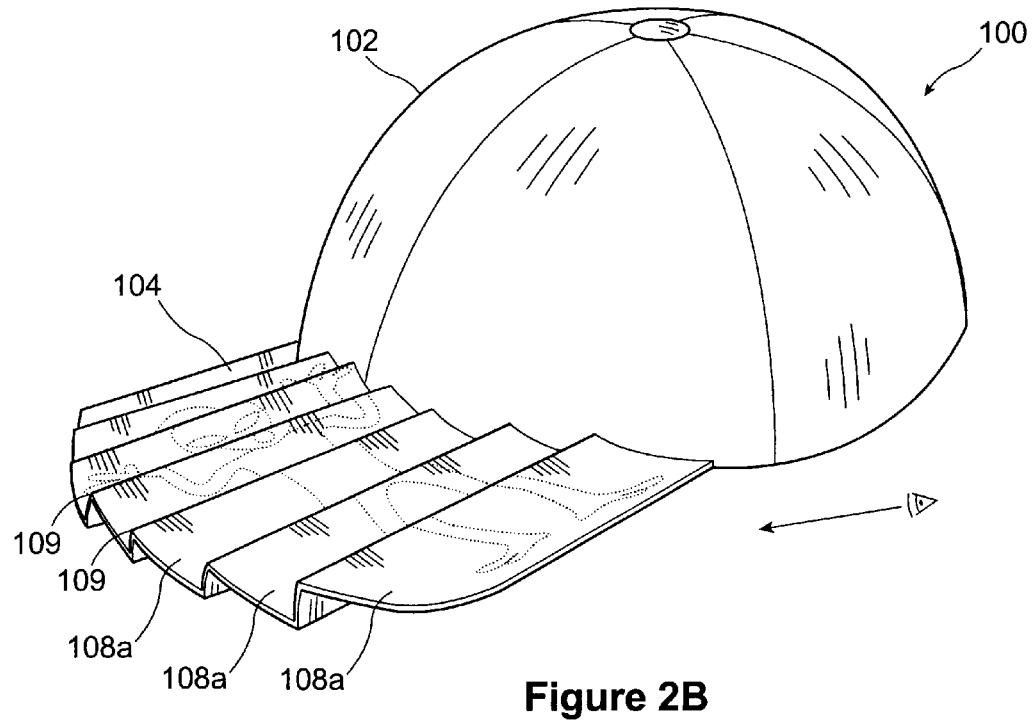
FIG. 2B is a perspective view of the top of a baseball-type cap depicted in FIG. 2A showing another composite image on the brim viewed from the opposite side of the cap.

As illustrated in FIG. 1A, the sections 106a of the first series 106 are viewable from a first direction in which the sections 108a of the second series 108 are not, and as illustrated by FIG. 1B, the sections 108a of the second series 108 are viewable from a second direction in which the sections 106a are not. The sections 106a, 108a of each series of sections 106, 108 carry images as shown in FIGS. 1A and 1B that are preferably related, or a composite image as shown in FIGS. 2A and 2B. Different symbols are used in FIGS. 1A and 1B to portray the different images. In the preferred embodiment, the first composite or individual images on the series of sections 106a is different from those on the series of sections 108a; however it is contemplated that composite or individual images can be the same for each series.

The baseball-type cap 100 depicted in FIGS. 2A and 2B is the same as the cap depicted in FIGS. 1A and 1B, except for the images, as discussed above. Thus, one composite image is presented in FIG. 2A when the cap is viewed from a first direction, and another composite image is presented in FIG. 2B when the cap is viewed from the opposite direction.

The caps depicted in FIGS. 1A, 1B, 2A and 2B as described above have images on the top of the brim 104. However, images are preferably also provided on sections 106b and 108b on the bottom of the brim. Such caps provide four composite images, or four sets of images, when viewed from four different directions.

Figure 3B:
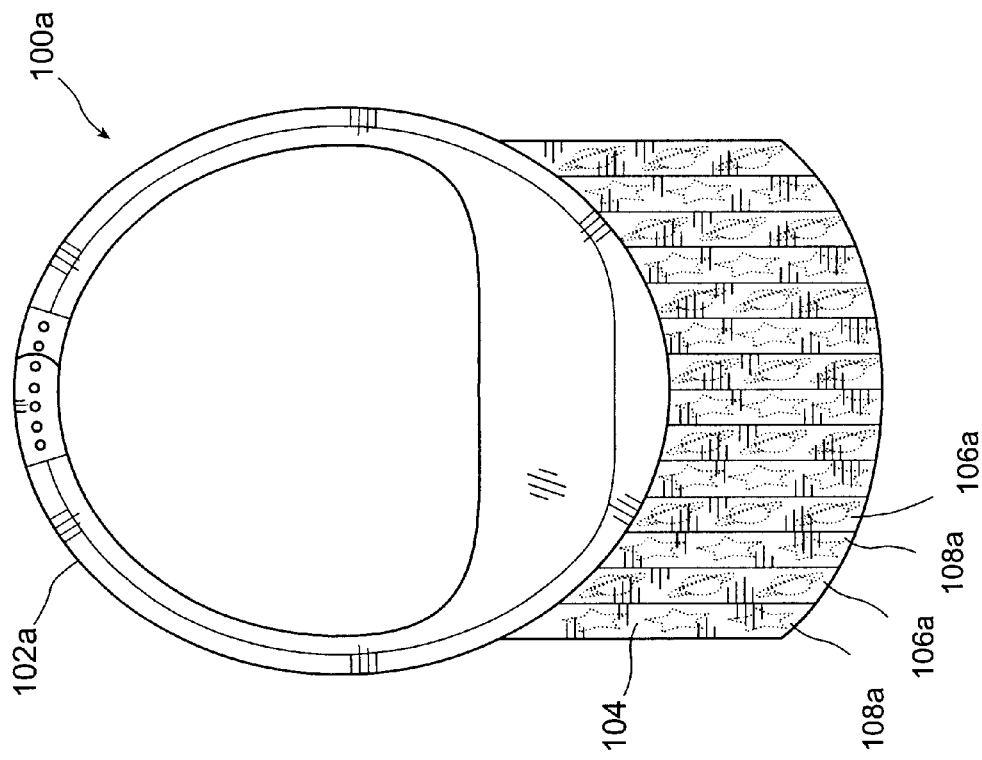
FIGS. 3A and 3B are top and bottom views, respectively, of a visor incorporating the invention.
Figure 3A:
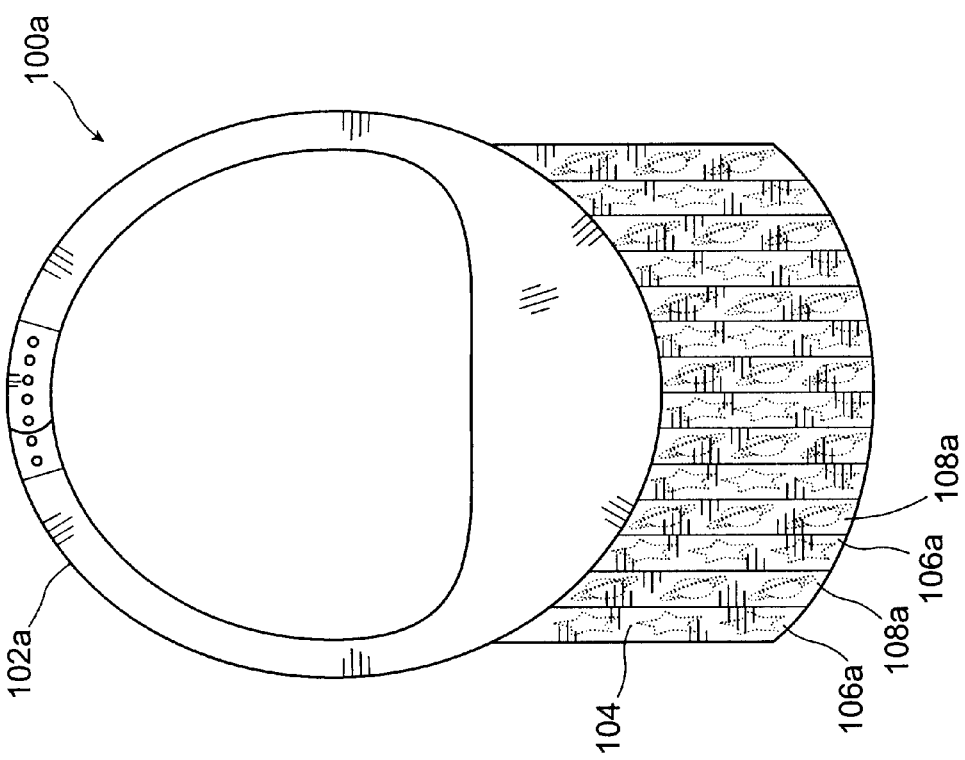

A visor 100a depicted in FIGS. 3A and 3B includes a brim 104 similar or the same as the brim 104 described above in connection with FIGS. 1A, 1B, 2A and 2B secured to a loop structure comprising at least a band 102a.

Figure 4A:
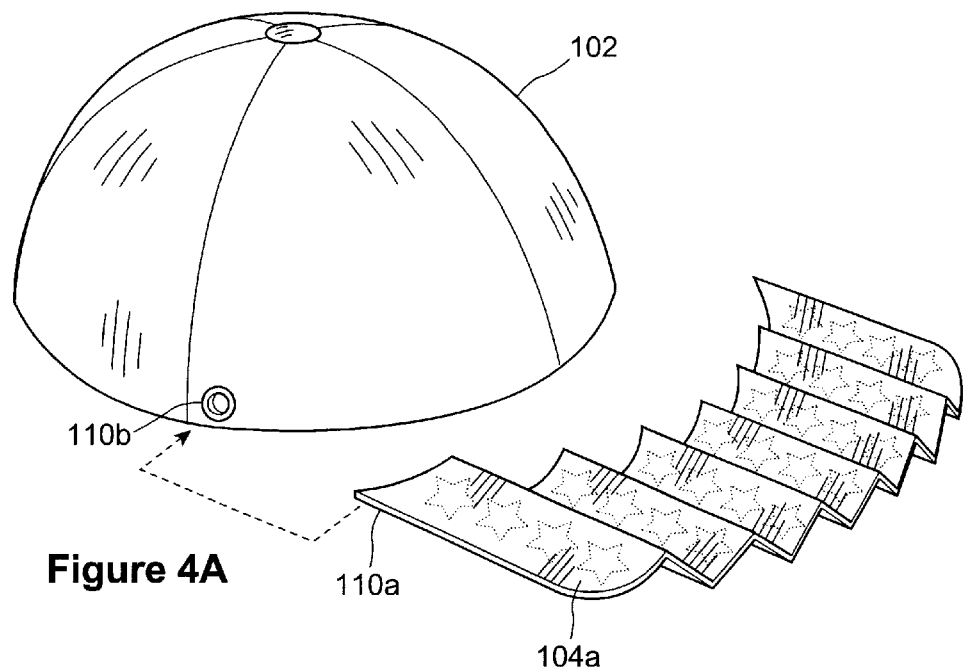
FIG. 4A is an exploded perspective view of a baseball-type cap incorporating the invention in which the brim is removable.
Figure 4B:
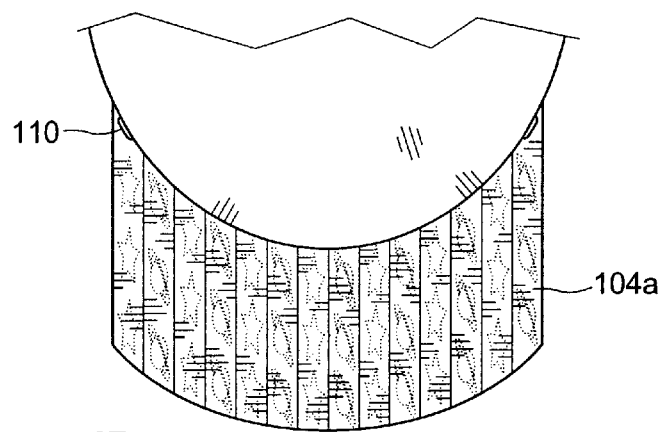
FIG. 4B is a bottom view of the brim portion of the baseball-type cap depicted in FIG. 4A.
Figure 4C:
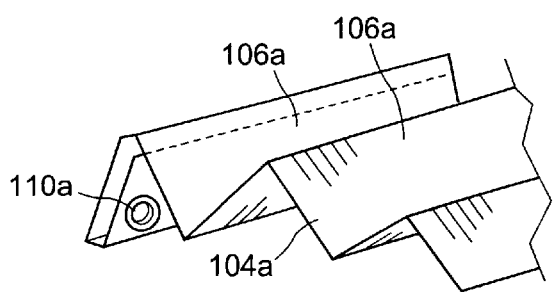
FIG. 4C is an enlarged perspective view of the top of the brim of the baseball-type cap depicted in FIG. 4A showing a snap structure for securing the brim to the cap.

In some embodiments, a wavelike brim 104a is removably secured to a loop structure 102, as illustrated in FIGS. 4A, 4B and 4C. The brim 104a may be secured to the loop structure 102 in any suitable manner. For example, a snap mechanism 110a, 110b may be used to releasably secure the brim 104a to the loop structure 102. In the preferred embodiment, the snap mechanism parts 110a on the brim 104a are located at the two ends of the brim; however they may be located in other places on the brim. Also, other fastener mechanisms may be used, for example so-called hook and loop fasteners (e.g., commercially available under the name Velcro).

The baseball-type cap 100b depicted in FIG. 5 comprises a cap section 102b, a brim panel 112 and a wave-like structure 104b that is releasably secured to the brim panel 112 in any suitable manner, for example, by snap mechanisms 110, a hook and loop fastener system, or by adhesive, etc. Wave-like structures 104b may be releasably secured to the top of brim 112, to the bottom, or to both the top and bottom. The wave-like structures 104a are similar to or the same as a brim 104.

Figure 6:
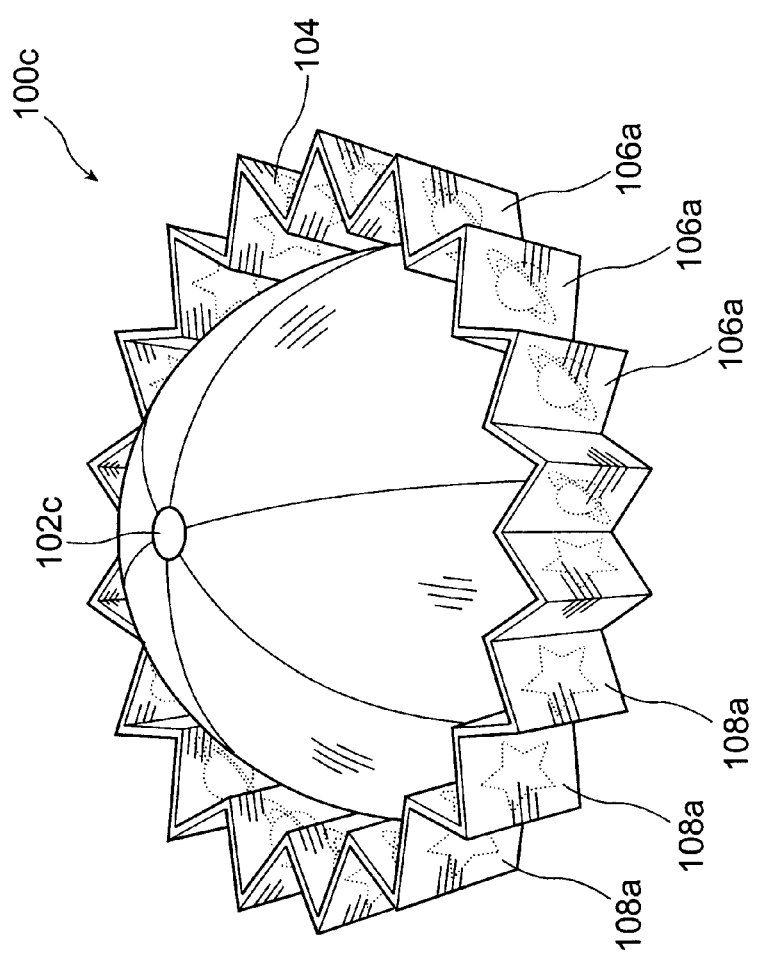
FIG. 6 is perspective view of a sailor-type hat incorporating the invention.

A sailor-type hat 100c incorporating the invention, depicted in FIG. 6, comprises a cap section 102c and a brim 104c attached to and extending in a closed loop about the periphery of the cap section. The brim 104c includes sections 106a, 108a that project substantially vertically when the hat 100c is worn. In this embodiment, all first series sections 106a face in the same first angular direction and all second series sections 108a face in the same second angular direction. All first series sections 106a face substantially clockwise about a substantially central axis and all second series sections 108a face substantially counterclockwise about the same substantially central axis. A first composite image or series of images is seen by viewing first series sections 106a from a first angle and a second composite image or series of images is seen by viewing the second series sections 108a from second angle.

Figure 7:
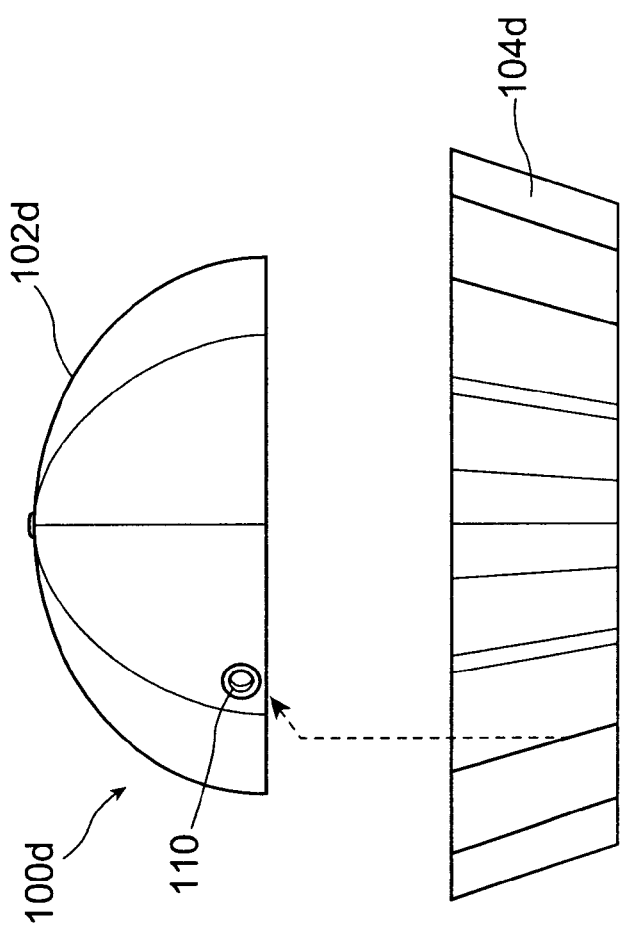
FIG. 7 is an exploded perspective view of a sailor-type hat incorporating the invention in which the brim is removably secured to the hat.
Figure 8:
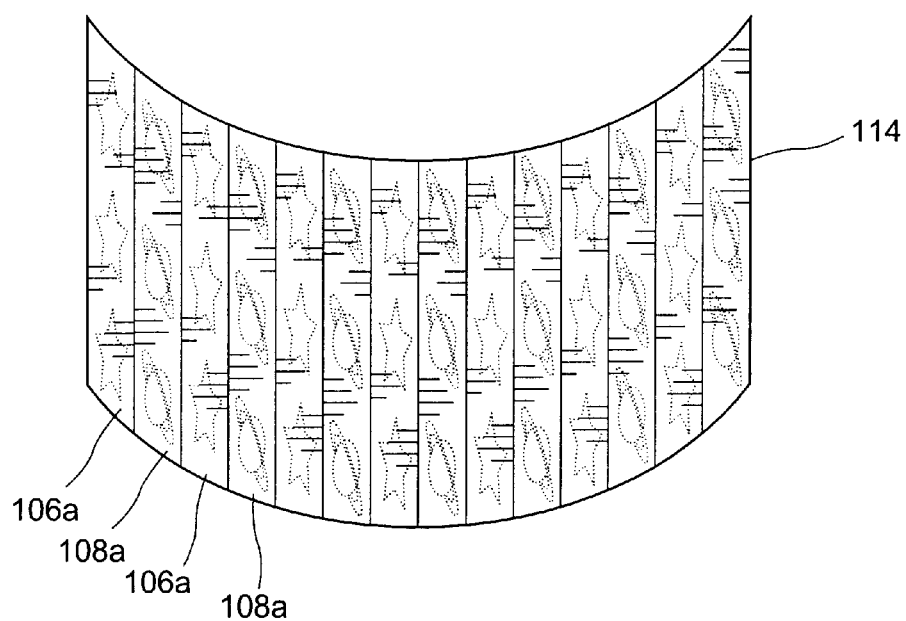
FIG. 8 is a top view of a sample display side of the flexible planar sheet.

The brim 104c of hat 100c is permanently attached to the cap section 102c. FIG. 7 depicts an embodiment of a sailor hat 100d that comprises a cap section 102d and a brim 104d that is releasably secured to the cap section by a suitable fastener system, for example those described above. As shown in FIG. 7, snap mechanisms 110 may be used.

Types of hats other than baseball-type, visors and sailor-type may incorporate the invention. Brims projecting horizontally from a cap section and extending entirely around the cap section, such as a Stetson-type hat or a fedora, or partially around the cap section may be provided with a wave-like structure as generally described above for a baseball-type cap. Those skilled in the art will be able to fabricate such hats from the disclosure herein.

The caps with removable brims or removable wave-like structures may be provided in kit form for assembly by consumers. A kit may include a flexible planar sheet 114 comprising an adhesive side and a display side, wherein the display side carries a series of sections 106a and 108a, as described above, for securing to a brim or to another sheet 114. The sheet 114 may be made of any suitable material, such as cardboard or plastic. In a preferred embodiment, the adhesive side has a peel-off backing that preserves the integrity of the adhesive. In an alternative embodiment, the kit includes one or more stiff wavelike structures (such as structure 104b depicted in FIG. 5) comprising a securable side and a display side, wherein the display side carries a series of sections 106a and 108a, as described above, and the securable side is secured, as described herein, to a brim panel that may be flat (e.g., brim panel 112 in FIG. 5) or a wave-like brim panel (not shown, but similar to brim 104 in FIG. 1A without the images). It is contemplated that wave-like structures supplied in kits are interchangeable.

For best visual effects, the sections in the various wave-like structures described above are preferably flat, of equal size, and in some cases arranged parallel to each other, with the sections of one series being orientated transversely (preferably an angle in the range of 30 to 60 degrees) to the sections of the other series.

The foregoing descriptions of specific embodiments of the present invention have been presented for purposes of illustration and description. They are not intended to be exhaustive or to limit the invention to the precise forms disclosed, and obviously many modifications and variations are possible in light of the disclosure herein. Those skilled in the art will appreciate that many modifications and variations may be made to the embodiments described herein without departing from the spirit or scope of the invention. The applicant intends that the claims cover all such modifications and variations, and equivalents thereof, permitted by the prior art.

What is claimed is:

1. A head apparel, comprising:
   a loop structure sized to engage a person's head;
   a brim secured to the loop structure, the brim comprising at least two series of interleaved sections arranged in a wave-like manner so that sections of each series are viewable by an observer from at least one direction and sections of respective series are viewable from at least one respective direction different from a direction from which sections of another series are viewable; and
   graphics on a plurality of sections of each series, the graphics defining a composite image or a plurality of related images that are viewable from the respective directions.

2. The head apparel of claim 1 wherein sections of the first series and sections of the second series are alternatingly interspersed with each other, adjacent sections each having a common edge or distinct adjacent edges that are substantially parallel.

3. The head apparel of claim 2 wherein the common edges of a substantial number of sections are substantially parallel to each other.

4. The head apparel of claim 1 wherein the loop structure comprises a cap section.

5. The head apparel of claim 4 wherein the head apparel is a baseball-type cap.

6. The head apparel of claim 4 wherein the head apparel is a sailor-type cap.

7. The head apparel of claim 1 wherein the head apparel is a visor.

8. The head apparel of claim 1 wherein the series of sections are connected to the loop structure and define the brim.

9. The head apparel of claim 1 wherein the brim comprises a brim panel connected to the loop structure and series of sections is secured to the brim panel.

10. The head apparel of claim 1 wherein the series of sections is removably secured to the brim panel.

11. The head apparel of claim 1 wherein the brim is removably secured to the loop structure.

12. The head apparel of claim 1 wherein the brim comprises two series of sections on a top of the brim and two series of sections on a bottom of the brim.

13. A head apparel, comprising:
    a loop structure sized to engage a person's head;
    a brim secured to the loop structure, the brim comprising at least two series of interleaved sections arranged on a top thereof in a wave-like manner so that sections of each series are viewable by an observer from at least one direction and sections of respective series are viewable from at least one respective direction different from a direction from which sections of another series are viewable, and at least two series of interleaved sections arranged on a bottom thereof in a wave-like manner so that sections of each series on the bottom are viewable by an observer from at least one direction and sections of respective series on the bottom are viewable from at least one respective direction different from a direction from which sections of another series on the bottom are viewable;

sections of the first series and sections of the second series on the top and on the bottom are alternatingly interspersed with each other, adjacent sections each having a common edge or distinct adjacent edges that are substantially parallel; and graphics on a plurality of sections of each series, the graphics defining a composite image or a plurality of related images that are viewable from the respective directions.

14. The head apparel of claim 13 wherein the common or distinct edges of a substantial number of sections are parallel to each other.

15. The head apparel of claim 13 wherein the loop structure comprises a cap structure.

16. The head apparel of claim 15 wherein the head apparel is a baseball-type cap.

17. The head apparel of claim 15 wherein the head apparel is a sailor-type cap.

18. The head apparel of claim 13 wherein the head apparel is a visor.

19. The head apparel of claim 13 wherein the series of sections are connected to the loop structure and define the brim.

20. The head apparel of claim 13 wherein the brim comprises a brim panel connected to the loop structure and the series of sections are secured to the brim panel.

21. The head apparel of claim 13 wherein the series of sections is removably secured to the brim.

22. The head apparel of claim 13 wherein the brim is removably secured to the loop structure.

23. A head apparel, comprising:

a loop structure sized to engage a person's head;

a brim removably secured to the loop structure, the brim comprising at least two series of interleaved sections arranged in a wave-like manner so that sections of each series are viewable by an observer from at least one direction and sections of respective series are viewable from at least one respective direction different from a direction from which sections of another series are viewable; and graphics on a plurality of sections of each series, the graphics defining a composite image or a plurality of related images that are viewable from the respective directions.

24. The head apparel of claim 23 wherein sections of the first series and sections of the second series are alternatingly interspersed with each other, adjacent sections each having a common edge or distinct adjacent edges that are substantially parallel.

25. The head apparel of claim 24 wherein the common edges of a substantial number of sections are parallel to each other.

26. A head apparel, comprising:

a loop structure sized to engage a person's head;

a brim secured to the loop structure, a wavelike structure comprising at least two series of interleaved sections arranged in a wave-like manner so that sections of each series are viewable by an observer from at least one direction and sections of respective series are viewable from at least one respective direction different from a direction from which sections of another series are viewable, the wave-like structure being removably secured to the brim; and graphics on a plurality of sections of each series, the graphics defining a composite image or a plurality of related images that are viewable from the respective directions.

27. The head apparel of claim 26 comprising a wave-like structure removably secured to a top of the brim and a wave-like structure removably secured to a bottom of the brim.

* * * * *